United States Patent [19]

Wiley

[11] 4,264,989
[45] May 5, 1981

[54] ARTIFICIAL LARYNX

[76] Inventor: Jack P. Wiley, P.O. Box 136, Linden, Tex. 75563

[21] Appl. No.: 86,735

[22] Filed: Oct. 22, 1979

[51] Int. Cl.$^3$ .............................................. A61F 1/20
[52] U.S. Cl. ...................................................... 3/1.3
[58] Field of Search ............................ 3/1.3; 181/126; 179/1 AL; 84/383 A

[56] References Cited

U.S. PATENT DOCUMENTS

| | | | |
|---|---|---|---|
| 1,836,816 | 12/1931 | Riesz | 3/1.3 |
| 1,840,112 | 1/1932 | Lane | 3/1.3 |
| 1,867,350 | 7/1932 | Burchett | 3/1.3 |
| 1,910,966 | 5/1933 | Riesz et al. | 3/1.3 |
| 2,405,850 | 8/1946 | Roberts | 3/1.3 |
| 2,405,851 | 8/1946 | Roberts | 3/1.3 |

*Primary Examiner*—Clifford D. Crowder
*Attorney, Agent, or Firm*—Merton H. Douthitt

[57] ABSTRACT

An improved acoustical artificial larynx comprises a sound chamber having an air inlet, an outlet for vibrating air, a mouth air discharge communicating with said outlet, a tone-producing element having an edge that is vibratable in the human voice range in response to air flow from said inlet, and spreader means for said vibratable edge. The latter element acts as a whispering control and has other utility. Additionally, the pitch can be modulated and, uniquely, the range of that modulation is adjustable.

10 Claims, 4 Drawing Figures

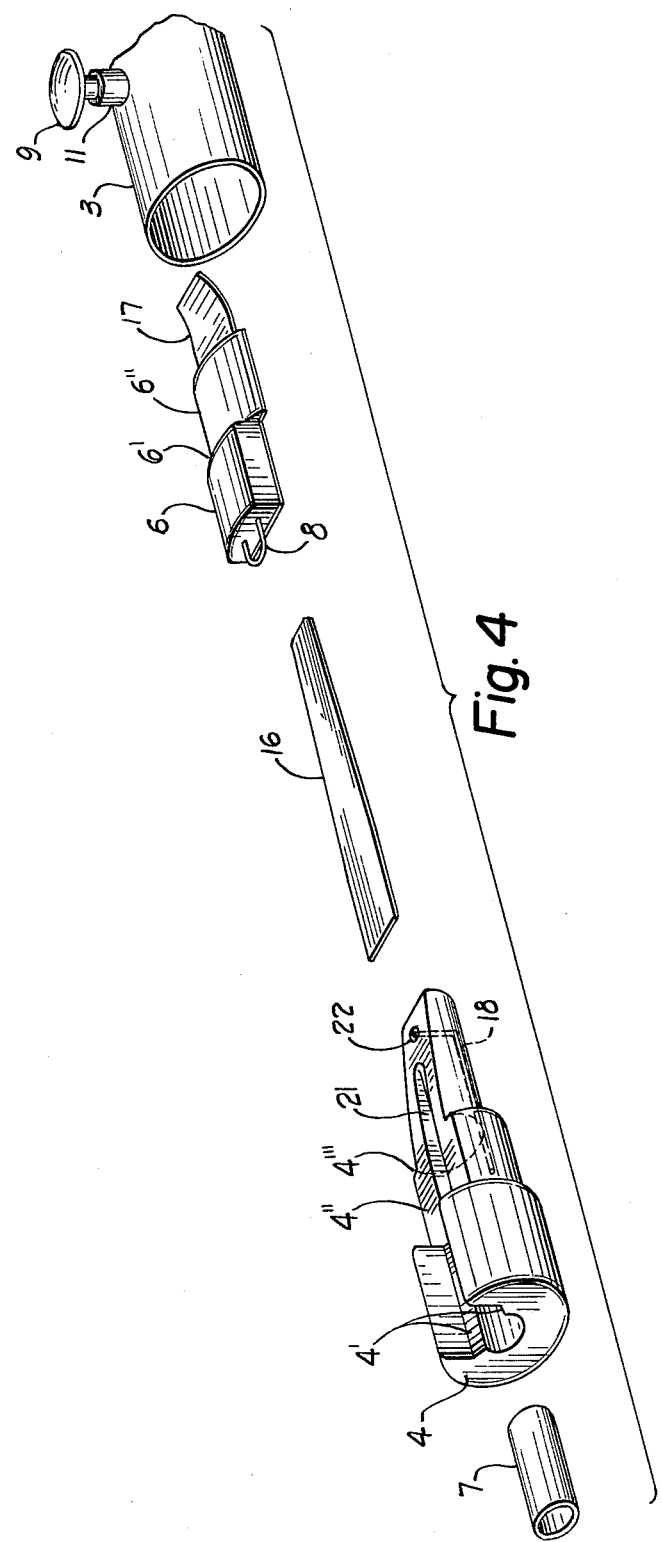

ARTIFICIAL LARYNX

This invention relates to an acoustical artificial larynx for restoring speech to a person who has had the natural larynx removed.

Heretofore various devices of this sort have been proposed. Representative are the following U.S. Pat. No. 1,836,816; 1,840,112; 1,867,350; 1,910,966 and 2,405,850. Advantages of the instant invention over such prior proposals include a novel whispering control, balance and general handiness for one-hand operation, both modulatable and fixed pitch adjustment with the range of modulation adjustable, and particularly easy disassembly and reassembly for cleaning and sanitation. This invention lends itself especially well to light, compact construction.

BROAD STATEMENT OF THE INVENTION

The artificial larynx of this invention comprises a sound chamber having an air inlet, an outlet for air, an air discharge element communicating with said outlet, a tone-producing element inside said chamber, said tone-producing element having an edge that is vibratable against a receptor element and vibratable in the human voice range in response to air flow from said inlet, and spreader means for spreading said vibratable edge away from said receptor element.

BRIEF DESCRIPTION OF THE DRAWING

FIG. 4 is a three dimensional exploded view of the invention.

DETAILED DESCRIPTION OF THE INVENTION

Figure 1:
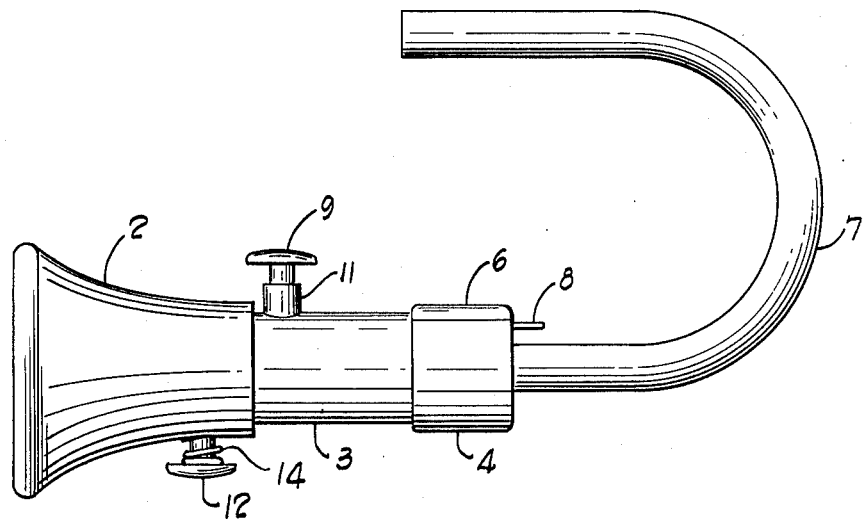
FIG. 1 is a side view of the invention.

FIG. 1 is a side view of a preferred embodiment of the instant artificial larynx. Item 2 is a stoma cover of plastic or, preferably, soft rubber that is adapted to fit snugly over the stoma area, i.e. the tracheal opening in the neck. The small end of stoma cover 2 fits tightly over one end of cylindrical metal sleeve 3, such sleeve being the lateral exterior wall of the sound chamber. Suitably sleeve 3 can be about 17 mm. in inside diamter, about 19 mm. in outside diameter, and about 4½cm. long. Into the other end of sleeve 3 is detachably plugged a subassembly of a reed (not visible in this view), a leaf spring (not visible in this view), channeled receptor 4, the exposed portion of which is depicted in this view, reed setter 6, the exposed portion of which is depicted in this view, and flexible mouth tube 7, the upstream end of which is held snugly between the exposed portion of receptor 4 and the root (fixed end) of said reed. Said upstream end of tube 7 acts as an outlet for vibrating air from the chamber. Tube 7 conducts such air into the mouth and there discharges it through one or more apertures near the end. Exhaled air passes between channeled receptor 4 and said reed, to vibrate the unsupported end of said reed. The vibrating air then passes through a channel in the receptor (said channel not depicted in this view), out flexible tube 7, and into the mouth where it is formed into speech in the speaker'mouth, nasal, and sinus cavities. Reed setter 6 fits into the exposed portion of said receptor to hold both said reed and said leaf spring firmly in operating position. The receptor and reed setter desirably are made of a hard plastic.

Item 8 is a staple embedded into and projecting from reed setter 6 to assist in moving such setter inwardly relative to the chamber to shorten the vibrating length of said reed or draw it outwardly to lengthen the vibrating length of the reed. thus giving a fixed pitch adjustment to said reed as well as to change the range of modulated pitch adjustment. Plunger 9 operates with finger pressure against the leaf spring to give modulated pitch adjustment. Plunger 9 is journalled through guide 11 that projects from sleeve 3 to give easy in-and-out motion with insignificant air leakage. Piston 12, spring-loaded to remain extended outwardly at rest, is likewise journalled through a guide (not visible in this view). Inward pressure on piston 12 acts to spread the vibratable portion (tip) of the reed from the channeled receptor, thereby permitting the user to whisper as well as to disengage the reed tip from the receptor when it is lightly stuck thereto by condensation or the like.

Figure 2:
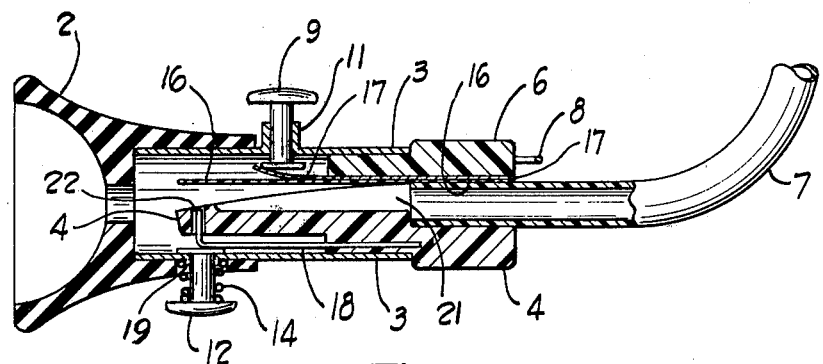
FIG. 2 is a vertical cross-section through the center of FIG. 1.

FIG. 2 is a vertical cross section through the center of FIG. 1, except that only the upstream portion of flexible tube 7 is depicted instead of all of it. Items 2, 3, 4, 6, 7, 8, 9, 11, 12, and 14 are and act as described above in connection with FIG. 1. From FIG. 2 it can be seen that one end of channeled receptor 4 extends inwardly into cylinder sleeve 3, as does one end of reed setter 6. Also extending inwardly into sleeve 3 is reed 16, typicaly a flat, thin, plastic strip overlapping channel 21 of receptor 4 and forming a gradually widening air aperture between the vibrating portion of such reed and the inward extension of said receptor bounding channel 21. Typically channel 21 is about 3 cm. long, about 3 mm. wide, about 3 mm. deep where it abuts the end of tube 7 and about 2 mm. deep at the other end. (The arrangement is broadly analogous to a clarinet mouthpiece fitted with a reed). Also rooted together with reed 16 and extending into sleeve 3 is leaf spring 17. Reed setter 6 holds spring 17 and reed 16 tightly together at their roots with the root of reed 16 pressing against the upstream end of tube 7 and slightly flattening it. Said end is fitted into the exterior portion of receptor 4.

Reed 16 is a piece of flat, thin (about 0.25 mm. or a little less), flexible thermoplastic, typically about 5.3 cm. long and tapering in width from 1 cm. at the root to about 7 mm. at the vibrating tip. It is readily replaceable with other similar reeds and not adhesively united to any other part. On the other hand, leaf spring 16 advantageously is adhesively united (glued) to the inside surface of reed setter 6 and extends outwardly therefrom about 1.3 cm. It is about 0.2 mm. thick and of corrosion-resistant springy metal chamfered slightly torwards the unsupported, depressible tip (the unsupported portion going from about 11 mm. wide at root end to about 9 mm. wide at the tip). Such unsupported portion bends away from the plane of reed 16 gradually. Pressure on plunger 9 pushes spring 17 against reed 16, and this shortens the vibrating portion of the reed gradually while raising its pitch also gradually. There should be minimum leakage in the instrument of vibrating air that should flow to the mouth. Accordingly, items 4, 6, 16, 17, and the upstream end of flexible tube 7 in service should be fitted quite well and held tighly together in a substantially leakproof manner when plugged as a subassembly into sleeve 3.

A special feature of this invention, alluded to in FIG. 1, is shown in its preferred structure in FIG. 2. Thus spring-loaded piston 12, when pushed inwardly depresses, spring wire 18. The root of wire 18 is embedded into receptor 4. The free end of wire 18 is bent upwardly to form a parting pin passing through tiny hole 22 in receptor 4. At rest, this pin does not touch reed 16 or interfere with its vibration. However, when whispering is desired, piston 12 is pushed against element 18 to propel the pin end portion thereof contact with reed 16, thereby spreading the vibrating tip more or less but very slightly away from the receptor against which it vibrates. This parting pin can be actuated to free the reed when it is stuck closed or slightly clogged.

Figure 3:
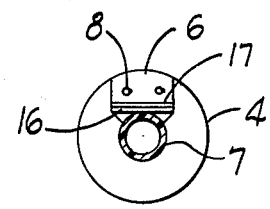
FIG. 3 is an enlarged end view with portions removed.

FIGS. 1 and 2 are drawn approximately to scale whereas FIG. 3 is enlarged for clarity. It depicts the exterior end view of the subassembly fitted together, with tube 7 and staple 8 arbitrarily being cut off substantially flush with the exterior end of channeled receptor 4. Thus, reed setter 6 sits into a slot in the top of receptor 4. Leaf spring 17 is glued to the bottom or reed setter 6, and the spring root presses flush against the up side of the root of reed 16. The bottom of such reed root presses against that upstream portion of tube 7 that is fitted into receptor 4 and is otherwise surrounded by such receptor. Advantageously such engaged tube part merely fits snugly without leakage about the exposed end of receoptor 4. Accordingly, it can be easily removed for cleansing or replacement. It also can be sealed, as with a cement, into said receptor end, at least temporarily when desired.

FIG. 4 is a three dimensional exploded view of the subassembly that is held together by being plugged into the end of sleeve 3, except that the discharge end of tube 7 into the mouth is not shown, but rather only the end which fits into receptor 4.

Reading arbitarily from left to right, the upstream end of tube 7 fits snugly into the outlet end of channeled receptor 4 that is exposed. Receptor 4 is of hard plastic with flat planes at interior level 4'. Extending from right to left is facing 4", which is essentially an extension of planes 4'. This facing starts from the left in essentially coplanar fashion with planes 4', but after second shoulder 4''' such facing gradually slopes away from the plane of reed 16 to form the lay for such reed. Item 21 is the channel in receptor 4 whence vibrating air is conducted to the outlet, through tube 7, and into the mouth.

Spring 18 is embedded at its left end to fix it into the external part of receptor 4; it is bent at the right hand end to form a pin which passes through hole 22 so that the tip of the pin at rest is just below being flush with the facing. The left hand end of plastic reed 16 rests on planes 4' and the left end of facing 4". The reed can be moved right or left somewhat to adjust its vibratable length. The left hand end of the reed can protrude from the exterior end of receptor 4 if necessary. Desirably the reed will cover all of channel 21 and extends to the right thereof.

Leaf spring 17 desirably is glued fairly permanently onto the bottom of reed setter piece 6. Staple 8 projects from the rear of piece 6. Piece 6 and leaf spring 17 fit into the exterior portion of receptor 4, thus making such spring press against the root of reed 16, which in turn is pressed against the inserted part of tube 7 shown in FIG. 4 and also against the left end of facing 4". The spring and reed setter can be moved slightly to the right or left slidably over on planes 4" and the part of facing 4" with which the reed is in contact. This changes the vibrting length of the reed as the clamped-down portion (root) of leaf spring 17 moves along the longitudal axis of the reed. Accordingly, the length of the reed from which pitch modulation is done by depressing the unsupported end of spring 17 against reed 16 can be adjusted. In other words, the range of such modulatable reed-pressing means thereby is made adjustable.

When these elements depicted in FIG. 4 are assembled for use, they are plugged in unitary manner into the end of sleeve 3, shown in fragmentary view at the far right. The end of sleeve 3 clamps the subassembly together and surrounds it almost up to the shoulder 6' of the reed setter piece (which is permitted a little right and left adjustment for helping to fix pitch and the modulatable range thereof as explained above).

To use this depicted embodiment of artificial larynx, the user places the free end of tube 7 into the mouth, preferably from the side and well back on the tongue. He holds bell-like stoma cover 2 over the stoma, then breathes the desired words while at the same time mouthing them.

Breathing through the unit should cause the reed to buzz. When the unit has not been used for a long period of time it sometimes will fail to operate. Blowing hard through it often helps to correct this. If the reed is warped or too much moisture has collected inside, it advantageously is disassembled, the parts dired with tissue, and tube 7 cleansed with a small plug of tissue pushed through it with a wire. If the reed is warped away from the channel of the receptor, thus letting too much air through tube 7, or is warped downwardly toward the receptor to unnecessarily throttle such air, turning the reed over in either case may help out (or the reed can be replaced). The thicker and stiffer the vibrating part of the reed, generally the higher the pitch. The reed itself can be moved to extend it farther into the sleeve for lowering the pitch or drawn back to shorten it and raise the pitch in a non-modulated way. Reed setter 6 also can be moved inwardly to raise the pitch of the reed or outwardly to lower it for an umodulated pitch adjustment.

The unit can be partly or almost completely disassembled for washing, scalding or otherwise sterilizing, e.g. with rubbing alcohol. Accordingly, all the materials of construction, plastic, rubber, metal or otherwise advantageously should be tolerant of and resistant to these treatments. Even well-chewed chewing gum or the like can be used temporarily to hold the reed in place when in use and to fill leaks, e.g. about the root area of the reed.

While the illustrated preferred embodiment of this invention has a tone-producing element that comprises a single reed vibratable against a channeled receptor, it should be evident that a double reed arrangement could be used with one reed vibrating against the other (analogously to a bagpipe reed). The channel therebetween then would conduct the vibrating air stream to a chamber outlet communicating with the mouth air discharge. Also possible would be a vibratory tone-producing element consisting essentially of a hollow, flat, soft rubber tube supported at its outlet end, with its unsupported end acting to vibrate. In fact, almost any tone-producing element having an edge that is vibratable in the human voice range is broadly suitable. Lower, masculine, tones are most favored for the instant instrument. Reeds preferably are of plastic, but also can be of cane or metal.

The spreader means for separating the vibrating reed from its receptor (or opposed reed tips from each other if a double reed is used) can also take alternative forms. Thus, where double opposed reeds or a flattened, flexible tubing is used to provide a plurality of vibratable edges, these can be spread or parted, e.g. by a pin or a tapered element inserted at the tip end of such vibrating elements.

The modulatable pitch-adjusting element need not be leaf spring 17 subject to pressure as shown, although this is believed to be a superior construction. Many mechanisms which can foreshorten or lengthen the vibrating portion of the reed gradually or in very tiny increments to modulate the pitch adjustment and thereby the pitch, would be adequate, e.g. hand-operated roller or slider devices readily movable up and down the reed at or near the base of the vibrating portion of the reed.

While button-topped, pressure-activated pistons and plungers are the preferred vibration-modulating actuators for this instrument, mechanical equivalents for the purpose (such as spring loaded levers mounted to draw a pin or a leaf spring outwardly at rest and release it for inward contact with the vibratable part of the reed) also are feasible in place of such plungers and pistons.

In order to breath in one simply can separate the stoma cover, e.g. item 2, slightly away from the neck. Where it is desired to have a longer term stoma connection, or to plug the air inlet directly into the stoma, it can be useful to have a breathing port cut into the sound chamber, e.g. into sleeve 3. Such port can be covered by a fingertip or a padded, levered cover that is spring-loaded to keep it normally closed. However, to utilize such port simultaneously with pitch and whisper modulator elements most likely would take three fingers, or a thumb and two fingers, advantageously using two hands. Having more than two-finger or a thumb-and-one-finger operation on the device can make it a bit complex to use, as with an ordinary telephone.

While the drawings depict the preferred embodiment of the invention in one orientation, it should be obvious that the plungers and pistons or other modulating actuators can be disposed about the periphery of the sound chamber in many different other orientations as necessary or desired, that the stoma cover need not be directly connected to the sound chamber, but rather the input air can be led from such connection through a tube, and further, the flexible outlet tube for vibrating air that goes into the mouth can be terminated to discharge air there differently and can be oriented differently relative to the modulating actuators, etc. without departure from the scope of this invention. Even the flexible tube for vibrating air can be more or less rigid without appreciable loss of utility. Accordingly, the invention should be restricted only by the appended claims.

Conventional moulded or extruded plastics and rubbers are particularly well suited for making most of the elements of the instant inventive construction, even some spring elements, and metals such as aluminum, stainless steels, copper, and brass obviously are useful for many of the elements also.

What is claimed is:

1. An artificial larynx comprising a sound chamber having an air inlet, an outlet for air, an air discharge element communicating with said outlet, a tone-producing element inside said chamber, said tone-producing element having an edge that is vibratable against a receptor element and vibratable in the human voice range in response to air flow from said inlet, and spreader means for spreading said vibratable edge away from said receptor element.

2. The artificial larynx of claim 1 wherein said tone-producing element comprises a reed vibratable against a channeled receptor which communicates with said outlet for vibrating air, and said spreader means is adjustabe for parting the vibrating portion of said reed from said receptor.

3. The artificial larynx of claim 2 wherein the spreader means is a reciprocatory means disposed to part said vibrating portion of the reed from said receptor in response to pressure delivered from said spreader means to said vibrating portion.

4. The artificial larynx of claim 3 wherein said spreader means comprises a manually despressible spring-loaded piston projecting through the outer periphery of said chamber for delivering parting pressure to the vibrating portion of said reed.

5. The artificial larynx of claim 1 which has means for adjusting pitch of the tone produced by said tone-producing element.

6. The artificial larynx of claim 5 wherein said tone, producing element comprises a reed vibratable against a channeled receptor which communicates with said outlet or air, and said means for adjusting pitch comprises manually-modulatable reed-pressing means disposed for gradually shortening and lengthening the vibrating portion of said reed, and the range of said reed-pressing means is adjustable along the longitudinal axis of said reed.

7. The artificial larynx of claim 6 wherein said reed-pressing means is a leaf spring projecting with and gradually and increasingly diverging from said reed, operating pressure on said spring is transmittable thereto from a plunger projecting through the outer periphery of said chamber, and the root of said leaf spring is adjustable along the longitudinal axis of said reed.

8. The artificial larynx of claim 7 wherein said spring, said reed, said channeled receptor, and a reed setter are held together as a disassemblable subassembly that is detachably plugged into a sleeve which constitutes part of the outer periphery of said sound chamber.

9. The artificial larynx of claim 8 wherein said spreader means comprises a manually-depressible, spring-loaded piston projecting through said sleeve and a parting pin inside said sleeve, said pin being disposed to pass through the channeled receptor and spread therefrom the vibrating portion of said reed in response to depression of said piston.

10. The artificial layrnx of claim 1 wherein said sound chamber air inlet has a stoma cover projecting immediately therefrom.

* * * * *